United States Patent [19]

Lyman et al.

[11] 4,012,288
[45] Mar. 15, 1977

[54] TISSUE CULTURE CLUSTER DISH

[75] Inventors: George F. Lyman, Weston; Alan Lowry, Canton, both of Mass.

[73] Assignee: Data Packaging Corporation, Cambridge, Mass.

[22] Filed: Oct. 6, 1975

[21] Appl. No.: 619,603

[52] U.S. Cl. .............................................. 195/139
[51] Int. Cl.² ......................................... C12K 1/10
[58] Field of Search .................................... 195/139

[56] References Cited

UNITED STATES PATENTS

| | | | |
|---|---|---|---|
| 3,165,450 | 1/1965 | Scheidt | 195/139 |
| 3,203,870 | 8/1965 | Andelin | 195/139 |
| 3,597,326 | 8/1971 | Liner | 195/139 |
| 3,729,382 | 4/1973 | Shaffer et al. | 195/139 |
| 3,886,047 | 5/1975 | Billups | 195/139 |
| 3,902,972 | 9/1975 | Beckford | 195/139 |

*Primary Examiner*—A. Louis Monacell
*Assistant Examiner*—Robert J. Warden
*Attorney, Agent, or Firm*—Wolf, Greenfield & Sacks

[57] ABSTRACT

A tissue culture cluster dish, having a lid which may be removably placed on a base having formed in it a plurality of wells for the placement and growth of tissue cultures; the wells having well bottoms which are transparent and flat for easy viewing of the well contents, the well bottoms being elevated above the plane in which the base makes contact with any horizontal planar surface upon which the base is placed; the base having ribbing which extends below and surrounds the well bottoms, the base further having a base rim of sufficient vertical extend for easy grasping and holding; the lid coming in contact with and being supported by the base only through protrusions upwardly extending from the base, thereby assuring atmospheric communication between the well interiors and the outside of the dish; the lid having ridges to prevent transfer of moisture from the area above one well to that above any other well; and the lid fitting on the base only in one orientation.

17 Claims, 7 Drawing Figures

U.S. Patent   Mar. 15, 1977   Sheet 1 of 2   4,012,288
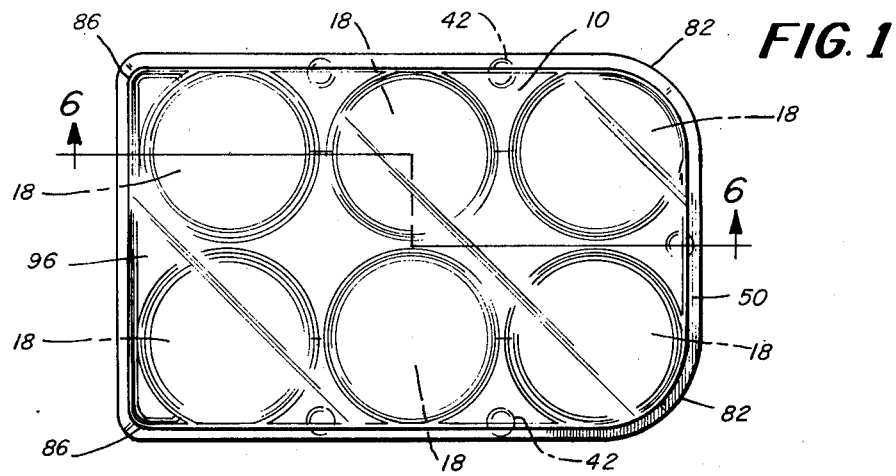
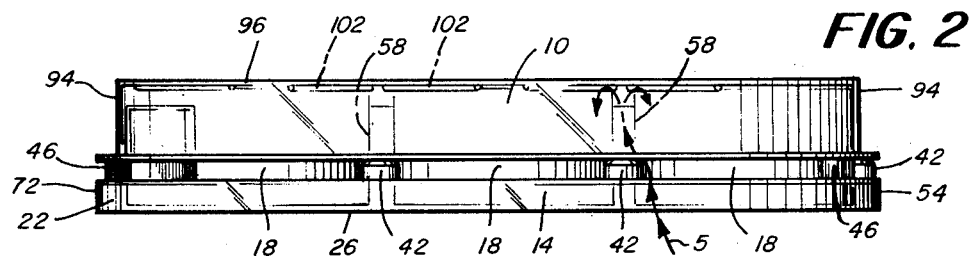
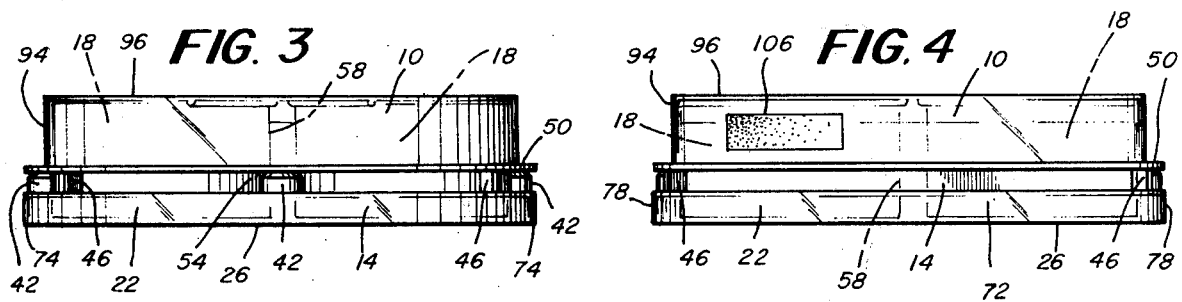
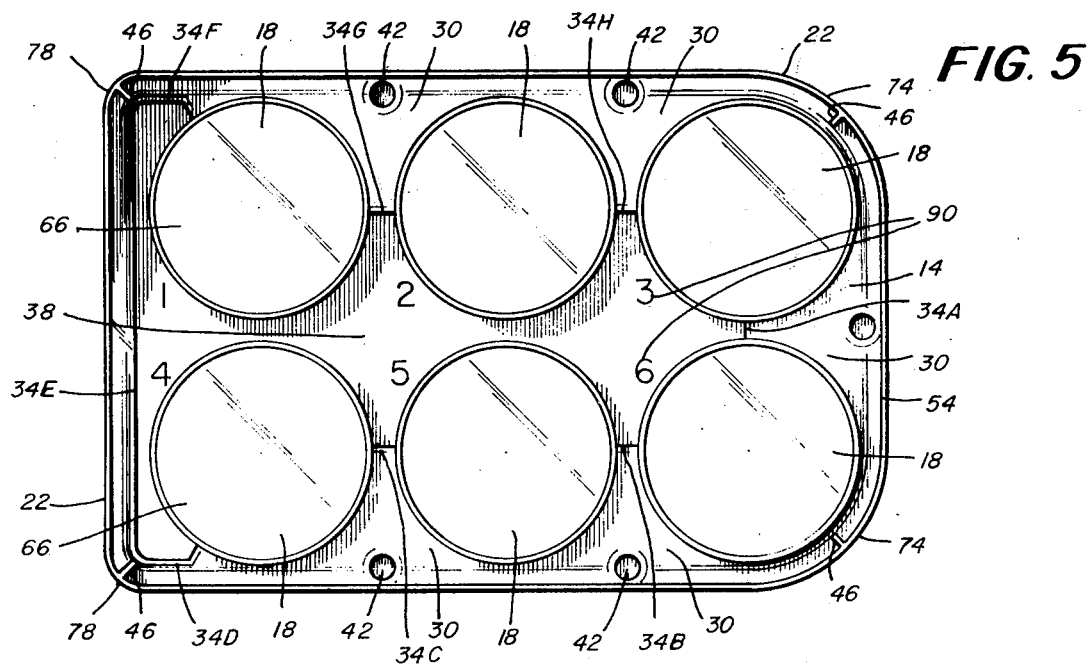

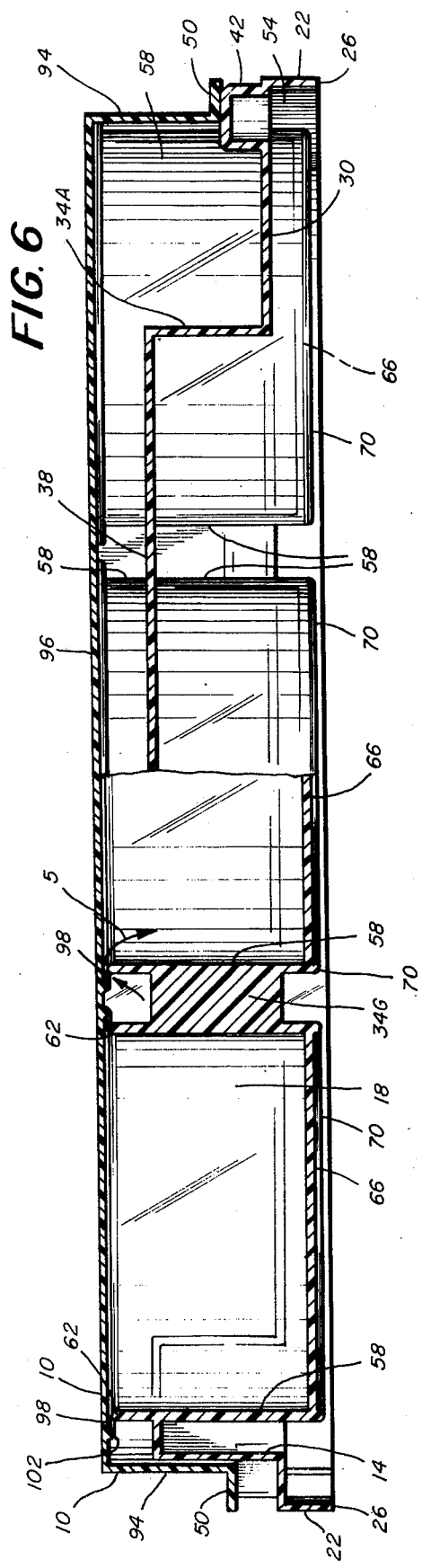
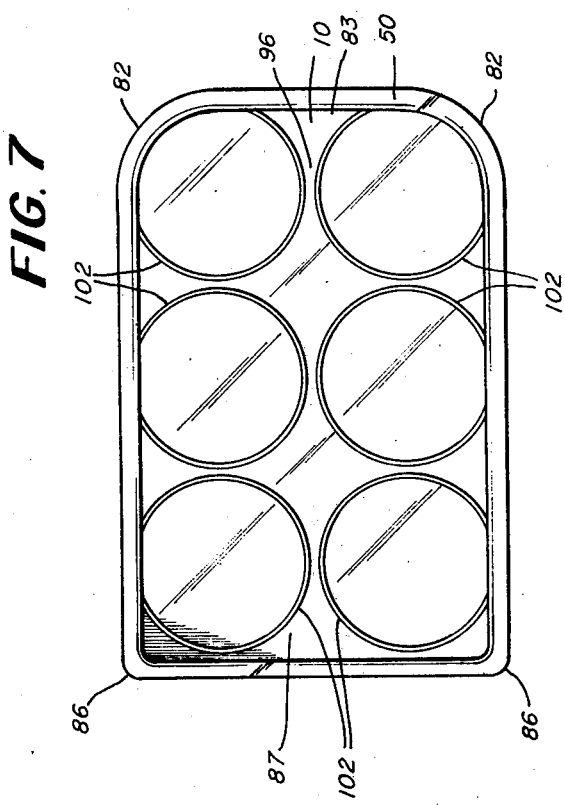

TISSUE CULTURE CLUSTER DISH

SUMMARY AND BACKGROUND OF THE INVENTION

The present invention relates to tissue culture dishes and more particularly to a dish having a plurality of wells in which tissue cultures may be grown for experimental or test purposes. Having such a plurality of wells for growth of separate cultures, a dish constructed according to the present invention provides the convenience of keeping together a number of correlated tests.

The dish of this invention is constructed of a clear transparent material, preferably plastic, for the facilitation of the viewing of the contents of each of the wells. The base of the dish has a rim which comes in contact with any supporting surface upon which the dish is placed. This rim is high enough for easy and secure grasping and holding by a user.

To guarantee continuous clear and undistorted viewing of the well contents, the well bottoms are flat and are located above the level at which the aforementioned base rim comes in contact with a supporting surface. This placement prevents contact between the well bottoms and the underlying surface and thereby reduces the possibility of scratching and soiling of the bottoms. The optical clarity of the well bottoms is further assured by the presence of ribs surrounding the well bottoms. These ribs prevent the scratching or soiling of the well bottoms that might arise out of contact with a user's fingers or hands.

The lid of the tissue culture dish has, like the base, a somewhat irregular profile when viewed from above. This feature guarantees that the lid can only be placed on the base in a single orientation and thereby reduces the possibility of inadvertent cross contamination of the contents of the various wells when the lid is removed during the running of a test or experiment.

The lid and base are constructed so that when in place on the base, the lid makes contact with the base only on small protrusions extending upwardly from the base. This feature assures that the atmosphere internal to any well is maintained with the same composition as the ambient atmosphere outside the tissue culture cluster dish.

The base is constructed without side walls on three sides; this further insures atmospheric communication between the wells and the ambient atmosphere and makes side viewing of the well contents somewhat clearer.

The lid has ridging extending down from the lower surface of its top. This ridging, when the lid is in place on the base, extends below the level at which the upper edges of the well walls lie. These ridges, which, along with sides of the lid, surround and segregate, from each other, the regions of the lower surface of the lid top lying above each of the wells prevent the transfer of condensed moisture from the region above one well to the region above any other. The ridges thereby reduce the likelihood of cross contamination of the wells due to tipping, etc.

A tissue culture cluster dish built according to this invention may have the further feature of numbering associated with the wells for ease in identification. For proper record keeping, a frosted area may be provided on the outside of the dish for the writing of data concerning the contents of the dish.

One object of the present invention is to provide a tissue culture dish having a plurality of wells for multiple or correlated tests or experiments.

Another object of the present invention is to provide a tissue culture dish with a plurality of wells in which communication between the interior of the wells and the outside atmosphere is assured even when the lid is in place.

Still another object of this invention is to provide a tissue culture dish having a plurality of wells, which is made of a transparent material for easy viewing of the contents of the wells.

A further object of this invention is to provide a tissue culture dish with a plurality of wells, the bottoms of each of which are flat and clear for easy and accurate viewing of the contents of each individual well.

Still a further object of this invention is to provide a tissue culture dish with well bottoms that are protected from scratching or soiling by contact with the surfaces on which the dish may be placed or by contact with a user's fingers or hands.

Another object of this invention is to provide a tissue culture dish, with a plurality of wells, in which the likelihood of cross contamination is reduced by having a lid which fits on the base in only one orientation.

Still another object of this invention is to provide a tissue culture dish, having a plurality of wells, in which the possibility of cross contamination is reduced by the presence in the lid of ridges which prevent the transfer of condensed moisture from the vicinity of one well to that of any other well.

A further object of this invention is to provide a tissue culture dish, having a plurality of wells, in which numbering is associated with each well for easy identification and on which a frosted area is provided for user notations.

These and other objects of the present invention will become clearer upon a consideration of the drawings and the detailed descriptions of particular embodiments of the present invention given below.

BRIEF FIGURE DESCRIPTION

FIG. 1 is a top view of a six well tissue culture cluster dish constructed according to this invention with its lid in place on the base.

FIG. 2 is a side view of the six well tissue culture cluster dish shown in FIG. 1.

FIG. 3 is a front view of the six well tissue culture cluster dish shown in FIG. 1.

FIG. 4 is a rear view of the six well tissue culture cluster dish shown in FIG. 1.

FIG. 5 is a top view of the base of the six well tissue culture cluster dish shown in FIG. 1 and with the cover removed.

FIG. 6 is a cross-sectional view of the six well tissue culture cluster dish taken along section line 6—6 of FIG. 1.

FIG. 7 is a bottom view of the lid of the six well tissue culture cluster dish shown in FIG. 1.

DETAILED DESCRIPTION

The tissue culture cluster dish shown in FIGS. 1–7 is composed of a removable lid 10 and base 14, both made of the same transparent plastic material. In the present embodiment six wells 18 are formed in base 14 in which separate and distinct cultures may be grown. It will of course be understood that a greater or smaller number of wells may be provided.

The base 14, which is of one piece molded construction, has a base rim 22 which, being downwardly extended below the rest of the base, comes, at its lower edge 26, into contact with a supporting horizontal surface upon which the culture dish may be placed. The base rim 14 in the embodiment shown is approximately ¼ inch high, which is of sufficient vertical extent for ease in handling by a user.

Viewed from above, the base 14 has a horizontal lower platform 30 which extends inwardly toward the center of the base from the base rim 22 to the sides 34A, 34B, 34C, 34D, 34E, 34F, 34G, 34H, of the upper platform 38 and the well walls 58. Located on the periphery of the lower platform are a plurality of support posts 42 and corner tabs 46. These support posts 42 and tabs 46 all are the same height so that they may support the lid 10 in a horizontal attitude by engaging, from below, its outwardly extending lip 50.

The upper platform 38 of the base 14 extends at its front, from the side 34A and the two wells 18 near the front 54, rearwardly to its rear side 34E. It is further delimited by side sections 34B, 34C, 34D, 34F, 34G, 34H and the well walls 58.

Extending upwardly, from the lower platform 30 near the periphery of the base 14 and from the upper platform 38 are the walls 58 of the wells 18. These cylindrical walls all extend to the same height above the upper platform 38 so that their upper edges 62 all lie in the same horizontal plane. The walls 58 all extend downwardly to join with the circular, horizontally planar well bottoms 66 to form the wells 18. These well bottoms 66 are made to be as optically flat as possible to provide for clear viewing of the contents of the wells 18 which they underlie.

It is to be observed that, as the base is formed in a single piece, each of the well walls 58, the upper platform 38, the lower platform 30, the platform sides 34 A–H, and the well bottoms 66 continuously merge with one another so that there is no atmospheric communication through the base 14. Each section of platform, wall or bottom which is part of the base is in the form of a relatively thin plastic sheet so that when viewed from below the base has hollow or empty areas beneath the upper platform 38.

Because of the importance of clear visibility through the well bottoms 66, the well walls 58 and well bottoms do not extend as far downwardly as the edge 26 of the base rim 22. This feature is best illustrated in FIG. 6. Being so elevated above the plane in which the base rim edge 26 lies, the well bottoms 66 do not come in contact with any horizontal surface upon which the tissue culture cluster dish may be placed and are thus protected against scratching or otherwise being soiled. As even further protection for the well bottoms 66, there are protruding ribs 70, arranged around each of them, which extend downwardly from the well walls 58, ending in a plane lying above that formed by the base rim edge 26. These ribs 70 do not themselves come in contact with any horizontal surface upon which the dish may be placed, but rather provide protection against scratching while the culture dish is being handled.

The base 14 has, notably, an identifiable front 54 and back 72. The front of the base has rounded corners 74 while its back has squared-off corners 78. As a further aid to the identification of the back of the base, the upper platform 38 extends in the back into its own squared off corners defined by the platform sides 34D, 34E and 34F. The lid 10 also has rounded off corners 82 at its front 83 and squared-off corners 86 at its back 87. Because of this shaping the lid 10 may only be fully lowered onto the base 14, to be supported by the support posts 42 and tabs 46, when its back corresponds to the back 72 of the base. Since there is only a single relative orientation for proper fitting of base 14 and lid 10, it is not possible accidently to contaminate the culture in one well 18 by bringing it in proximity with that area of the lid 10 which has previously been near the culture located in a different well 18.

As a further aid to the user the preferred embodiment illustrated has numbering 90 inscribed into the upper platform 38 of the base proximate to each well 18 in order to facilitate identification and cataloguing of the culture which may be placed therein.

The lid 10 has vertical sides 94 extending upwardly from the outwardly extended lip 50 to a height such that when the lid is in place on the base 14, being supported by virtue of the engagement of the lip 50 by the support posts 42 and tabs 46, the portions of the horizontally planar lower surface of the lid top 96 lying vertically above the well walls 58 do not engage the upper edges 62 of these walls, but, rather, leave small gaps 98 through which the well interiors communicate with the spaces between the lid 10 and the upper and lower platforms, 38 and 30, of the base 14. By virtue of the lid 10 being supported on the posts 42 and tabs 46, communication also exists between the outside atmosphere and the spaces above the platforms 30 and 38 even when the lid 50 is in place. Because of this communication and the existence of the gaps 98, the atmosphere in the wells 18 is maintained at concentrations equivalent to those in the ambient atmosphere outside the tissue culture cluster dish. Since the base has no straight side walls on its two sides and at its front 54 to engage with the sides 94 of the lid 10, no accidental sealing can occur which destroys the communication between the wells 18 and the outside atmosphere. Arrow 5 shows paths by which atmospheric access to the wells can be gained from outside the dish even with the lid in place.

Extending slightly downwardly from the lower surface of the lid top 96 are protruding circular ridge segments 102 which, when the lid 10 is in place on the base 14, extend around and outside the upper edges 62 of the well walls 58. The lower extremities of these ridges 102 lie, when the lid is placed on the base, in a horizontal plane lower than that in which the well wall edges 62 lie. As these circular ridge segments 102 have a greater radius of curvature than the circles formed by the well wall edges 62, their presence does not impede the atmospheric communication between the spaces inside and outside the wells.

In the use of these culture dishes, condensation, ultimately arising out of the presence of moisture in the material placed in the wells 18 for growth, forms on the lower surface of the top 96 of the lid in the regions just above the individual wells. The circular ridge segment 102 and the section of the vertical sides 94 of the lid 10 arranged around a particular well 18 completely surround the upper edge 62 of the well wall 58 of the given well and thereby prevent the condensed moisture which forms on the lid top 96 above that well from transferring over to and contaminating any other well.

The use of the tissue culture cluster dishes involves the introduction into the wells of samples mixed or combined with an appropriate nutrient bearing medium as well as various test chemicals, etc. The growth adheres to the plastic walls 58 and bottoms 66 of the wells 18. The sample in each well 18 is viewed through its well bottom 66 and through the portion of the lid top 96 lying above the well. This viewing is facilitated by the previously noted design features which protect the optically flat and clear well bottoms from inadvertent scratching. Since the base 14 has no peripheral walls at its front or along its two sides, side viewing distortion is minimized to facilitate examination of the material in the wells.

Because the protruding rings 102 on the lid significantly reduce the possibility of cross contamination, the lid may be removed during the course of an experiment or test, without danger of loss of valuable data, to inject nutrients or other material into the wells. The previously mentioned orientational requirements for proper fitting of lid 10 and base 14 further minimize the possibility of inadvertant contamination as well.

For the convenience of a user there is provided a frosted area 106 on the lid side 94 at its rear. This frosted area may be marked by the user to identify the samples or tests in the wells 18, each of which has associated numbering 90.

It will be clear to the reader having knowledge of the art that the specific embodiments discussed herein are not the only possible constructs that can be made according to this invention. Many other features not shown in the described embodiments should be obvious to those ordinarily skilled in the art and are within the spirit and scope of this invention.

What is claimed as this invention is:

1. A tissue culture cluster dish assembly comprising:
   a base having formed within it a plurality of wells for receiving materials,
   said wells formed in said base having flat bottoms for distortion free viewing, by a user, of the material received, and undergoing change, in said wells,
   said base having a front end and a back end;
   a lid for covering said base and the wells therein,
   said lid having a front end and back end,
   said lid being removably locatable on said base,
   said lid and said base being formed of a transparent material,
   said base having a base rim running around said base,
   said base rim having a lower edge which constitutes the lowest extremity of said base and which lies in a plane so that said base may be supported thereon when placed upon a planar surface,
   said flat bottoms of said wells lying in a plane elevated above and parallel to the plane in which said lower edge of said base rim lies so that said well bottoms cannot be scratched or soiled by making contact with any planar horizontal surface upon which said base may be placed,
   said wells formed in said base each having vertical well walls,
   said well walls each having upper edges which constitute the upper extremities of said base and which all lie in the same plane which is parallel to that in which said lower edge of said base rim lies,
   said well walls having, at their bottoms, ribs extending downwardly below the plane in which said well bottoms lie,
   said ribs running around the peripheries of said well bottoms thereby reducing the likelihood of the scratching and soiling of the lower surfaces of said well bottoms when said tissue culture cluster dish is being handled.

2. A tissue culture cluster dish assembly as described in claim 1, further characterized by
   said base having a plurality of upwardly extending protrusions having upper extremities all lying in a plane parallel to and above that in which the lower edge of said base rim lies,
   said lid having a lower lip, lying in a plane and constituting the lower extremity of said lid, for engagement with and support from below by said upper extremities of said protrusions in said base,
   said base having no side walls on at least its two sides so that viewing from the side through the lid is not hindered and inadvertend sealing cannot occur,
   said lid, when in place on said base, having contact with said base only by its engagement with said protrusions in said base,
   said wells having interiors which atmospherically communicate with the atmosphere outside said tissue culture cluster dish through the spaces between said protrusions in said base below the plane in which the upper extremities of said protrusions lie.

3. A tissue culture cluster dish as described by claim 2 further characterized by
   said base having substantially rounded corners at its front end and substantially squared corners at its back end,
   said lid having substantially rounded corners at its front end and substantially squared corners at its back end so that said lid may only fit on said base when said back and front of said lid correspond with said back and front of said base,
   said base having identifying numbering permanently associated with each of said wells.

4. A tissue culture cluster dish assembly as described in claim 2 further characterized by
   said lid having a lid top lying in a plane parallel to and above that in which said lip of said lid lies,
   said lid top being transparent for viewing from above of the contents of said wells,
   said lid having downwardly extending lid sides running between said lid top and said lid lip.

5. A tissue culture cluster dish assembly as described by claim 4 further characterized by
   said base having substantially rounded corners at its front end and substantially squared corners at its back end,
   said lid having substantially rounded corners at its front end and substantially squared corners at its back end so that said lid may only fit on said base when said back and front of said lid correspond with said back and front of said base,
   said base having identifying numbering permanently associated with each of said wells.

6. A tissue culture cluster dish assembly as described in claim 5 further characterized by
   said base having a plurality of upwardly extending protrusions having upper extremities all lying in a plane parallel to and above that in which the lower edge of said base rim lies,
   said lid having a lower lip, lying in a plane and constituting the lower extremity of said lid, for engagement with and support from below by said upper extremities of said protrusions in said base, said base having no side walls on at least its two sides so that viewing from the side through the lid is not hindered and inadvertent sealing cannot occur, said lid, when in place on said base, having contact with said base only by its engagement with said protrusions in said base.

7. A tissue culture cluster dish assembly as described in claim 6 further characterized by said base having substantially rounded corners at its front end and substantially squared corners at its back end, said lid having substantially rounded corners at its front end and substantially squared corners at its back end so that said lid may only fit on said base when said back and front of said lid correspond with said back and front of said base, said base having identifying numbering permanently associated with each of said wells.

8. A tissue culture cluster dish assembly as described in claim 6 further characterized by said lid having a lid top lying in a plane parallel to and above that in which said lip of said lid lies, said lid top being transparent for viewing from above of the contents of said wells, said lid having downwardly extending lid sides running between said lid top and said lid lip.

9. A tissue culture cluster dish assembly as described in claim 8 further characterized by said base having substantially rounded corners at its front end and substantially squared corners at its back end said lid having substantially rounded corners at its front end and substantially squared corners at its back end so that said lid may only fit on said base when said back and front of said lid correspond with said back and front of said base, said base having identifying numbering permanently associated with each of said wells.

10. A tissue culture cluster dish assembly as described in claim 4, further characterised by said lid top having downwardly protruding ridges, extending from the under surface of said lid top, which, together with portions of said lid side, surround said upper edges of said well walls thereby segregating from each other those portions of lid top lying above each of said wells when said lid is in place on said base, said ridges downwardly extending so that their lower extremities lie in a plane parallel to and below the plane in which said lid top lies, said plane in which said lower extremities of said protruding ridges lie being, when said lid is in place on said base, below the plane in which said upper extremities of said well walls lie, thereby preventing the transfer of moisture forming on the portion of the lower surface of said lid top lying above one of said wells to that portion of said lower surface of said lid top lying above any other well.

11. A tissue culture cluster dish assembly as described by claim 10 further characterized by said base having substantially rounded corners at its front end and substantially squared corners at its back end, said lid having substantially rounded corners at its front end and substantially squared corners at its back end so that said lid may only fit on said base when said back and front of said lid correspond with said back and front of said base, said base having identifying numbering permanently associated with each of said wells.

12. A tissue culture cluster dish assembly as described by claim 11 further characterized by said base rim having a vertical extent of the order of a quarter of an inch or more for ease in grasping and holding by a user.

13. A tissue culture cluster dish assembly as described in claim 10 further characterized by said base rim having a vertical extent of the order of a quarter of an inch or more for ease in grasping and holding by a user.

14. A tissue culture cluster dish assembly as described by claim 1 further characterized by said base having substantially rounded corners at its front end and substantially squared corners at its back end, said lid having substantially rounded corners at its front end and substantially squared corners at its back end so that said lid may only fit on said base when said back and front of said lid correspond with said back and front of said base, said base having identifying numbering permanently associated with each of said wells.

15. A tissue culture cluster dish assembly comprising:

a base having formed within it a plurality of wells for receiving materials, and said base having a front end and a back end;

a lid for covering said base and the wells therein, said lid having a front end and back end, said lid being removably locatable on said base, said lid and said base being formed of a transparent material, said base having substantially rounded corners at its front end and substantially squared corners at its back end, said lid having substantially rounded corners at its front end and substantially squared corners at its back end so that said lid may only fit on said base when back and front of said lid correspond with said back and front of said base.

16. A tissue culture cluster dish assembly as characterized in claim 15 further characterized by said base having identifying numbering permanently associated with each of said wells.

17. A tissue culture cluster dish assembly comprising:

a base having formed within it a plurality of wells for receiving materials, said wells formed in said base having flat bottoms for distortion free viewing, by a user, of the material received, and undergoing change, in said wells, said base having a front end and a back end;

a lid for covering said base and the wells therein, said lid having a front end and back end, said lid being removably locatable on said base, said lid and said base being formed of a transparent material, said base having a base rim running around said base, said base rim having a lower edge which constitutes the lowest extremity of said base and which lies in a plane so that said base may be supported thereon when placed upon a planar surface, said flat bottoms of said wells lying in a plane elevated above and parallel to the plane in which said lower edge of said base rim lies so that said well bottoms cannot be scratched or soiled by making contact with any planar horizontal surface upon which said base may be placed, said base having a plurality of upwardly extending protrusions having upper extremities all lying in a plane parallel to and above that in which the lower edge of said base rim lies, said lid having a lower lip, lying in a plane and constituting the lower extremity of said lid, for engagement with and support from below by said upper extremities of said protrusions in said base, said base having no side walls on at least its two sides so that viewing from the side through the lid is not hindered and inadvertent sealing cannot occur, said lid, when in place on said base, having contact with said base only by its engagement with said protrusions in said base.

* * * * *